United States Patent
Weibel et al.

(10) Patent No.: US 9,711,317 B2
(45) Date of Patent: Jul. 18, 2017

(54) AIR IONIZATION MODULE

(71) Applicant: LK Luftqualität AG, Lucerne (CH)

(72) Inventors: Beda Weibel, Schwyz (CH); Michael Oswald, Lucerne (CH)

(73) Assignee: LK Luftqualität AG, Lucerne (CH)

( * ) Notice: Subject to any disclaimer, the term of this patent is extended or adjusted under 35 U.S.C. 154(b) by 46 days.

(21) Appl. No.: 14/891,681

(22) PCT Filed: May 26, 2014

(86) PCT No.: PCT/EP2014/060812
§ 371 (c)(1),
(2) Date: Nov. 17, 2015

(87) PCT Pub. No.: WO2014/191346
PCT Pub. Date: Dec. 4, 2014

(65) Prior Publication Data
US 2016/0093461 A1    Mar. 31, 2016

(30) Foreign Application Priority Data

May 29, 2013  (DE) .................. 10 2013 210 114

(51) Int. Cl.
*H01J 7/24* (2006.01)
*H05B 31/26* (2006.01)
(Continued)

(52) U.S. Cl.
CPC .............. *H01J 27/022* (2013.01); *A61L 9/22* (2013.01); *B01D 53/323* (2013.01); *F24F 3/166* (2013.01);
(Continued)

(58) Field of Classification Search
None
See application file for complete search history.

(56) References Cited

U.S. PATENT DOCUMENTS

| 4,188,530 A | 2/1980 | Miller | |
| 6,002,573 A * | 12/1999 | Partridge | .................. H05F 3/04 361/213 |
| 2006/0203416 A1* | 9/2006 | Taylor | ...................... B03C 3/32 361/230 |

FOREIGN PATENT DOCUMENTS

| EP | 1348448 A1 | 10/2003 |
| GB | 1177891 A | 1/1970 |
| WO | 2005029924 A1 | 3/2005 |

* cited by examiner

*Primary Examiner* — Anh Tran
(74) *Attorney, Agent, or Firm* — Michael Soderman

(57) ABSTRACT

The invention relates to air ionization modules with ionization tubes removably arranged in mounts and to a support comprising the mounts. The air ionization modules are characterized in particular in that as little condensation as possible occurs while enriching an air flow with ions. For this purpose, the support has two mutually spaced plates, a first plate being an assembly plate and a second plate being a circuit board comprising the mounts. Furthermore, a body made of a heat-insulating material is located between the plates such that the second plate is arranged so as to be heat-insulated relative to the first plate. The air ionization module is used to generate ions in an air flow for at least one inner room of a building. Ionized air leads to a separation of multiple odor-causing molecules, an eradication of microorganisms, a degradation of volatile gaseous hydrocarbons, and a reduction of the oxide potential of the air, for example. In this manner, a comfortable, near-natural air is produced in the room supplied with the air.

11 Claims, 3 Drawing Sheets

(51) Int. Cl.
  *H01J 27/02*    (2006.01)
  *A61L 9/22*     (2006.01)
  *F24F 3/16*     (2006.01)
  *H01T 23/00*    (2006.01)
  *B01D 53/32*    (2006.01)
(52) U.S. Cl.
  CPC ........ *H01T 23/00* (2013.01); *B01D 2257/708* (2013.01); *B01D 2257/91* (2013.01); *B01D 2259/4508* (2013.01); *F24F 2003/1682* (2013.01)

AIR IONIZATION MODULE

CROSS REFERENCE TO RELATED APPLICATIONS

This application is the U.S. national stage of International Application No. PCT/EP2014/060812, filed on May 26, 2014, and claims the benefit thereof. The international application claims the benefits of German Application No. DE 102013210114.7 filed on May 29, 2013; all applications are incorporated by reference herein in their entirety.

BACKGROUND

The invention relates to air ionization modules with ionization tubes removably arranged in mounts and a support with the mounts.

The fact that room air and therefore the air that is breathed can be treated with ionization devices is known. In so doing, bacteria and other germs are killed and large molecules are broken up into small-molecule fragments. Complex and large molecules are aromatic substances, among other things, so odors can be eliminated with air ionization. Furthermore, microorganisms in the air can be effectively reduced.

Electrical fields between two electrodes with voltage potentials are used in ionization devices to generate ions from impact ionization via gas discharges. Ionization tubes in the form of glass tubes with an internal electrode and an external electrode are used in a known way for this; a coaxial structure exists. If an electrical voltage that is sufficiently high for a gas discharge is applied, the glass of the wall forms a dielectric in which there is a large electrical field. The air passing through is enriched with ions. A drawback here is that ozone is created above a certain voltage that increases with an increase in the voltage.

A method for treating air with ions and a device for carrying out the method are known from the document DE 43 34 956 C2; the long-term stability of an ionization device is increased. The main point to note is an avoidance of increased ozone creation. Sensors in the form of an air-quality sensor, an air-flow sensor and a humidity sensor are used for this. The contamination of ozone in the incoming air can increase to an undesirable level and lead to limit values being exceeded from both external interference sources, for instance in the case of smog, temperature inversion, a thunderstorm and external energy fields, and internal interference sources via the operation of electrical devices.

A method of treating air with ions and a device for carrying out the method are described in the document DE 100 07 523 C2; an ozone sensor is additionally used to determine the ozone content. These documents do not go into the problems of the condensation of water brought about by a temperature difference between the surrounding air and, for example, cooled incoming air.

SUMMARY

The invention relates to an air ionization module with ionization tubes removably arranged in mounts and a support with the mounts. The support has two plates spaced apart from one another, wherein a first plate is a mounting plate and a second plate is a circuit board with the mounts. An element made of thermally insulating material is located between the plates so that the second plate is thermally insulating vis-a-vis the first plate.

DETAILED DESCRIPTION

The invention specified in claim 1 is based on the task of creating a compact air-ionization module to enrich an air flow with ions without condensation to a very great extent.

This problem is solved with the features specified in claim 1.

The air-ionization modules with ionization tubes removably arranged in mounts and a support with the mounts especially stand out because there is no condensation to a very great extent when the air flow is enriched with ions.

The support has two plates that are spaced apart with regard to one another for this; a first plate is a mounting plate and a second plate is a circuit board with the mounts. Furthermore, an element made of thermally insulating material is located between the plates, so the second plate is thermally insulated vis-a-vis the first plate.

The air ionization module serves to generate ions in an air flow for at least one interior room of a building. Ionized air leads, as an example, to a breakdown of odor-producing molecules, to a destruction of microorganisms, to a breakdown of gaseous, volatile hydrocarbons and to a reduction of the oxide potential of the air. Comfortable, near-natural air is created in the impacted room because of that.

The ionization tubes that are used in the process serve to generate the ions via corona discharges. That takes place via a high alternating electrical voltage applied to the ionization tubes. A known ionization tube has an anode and a grid-shaped cathode that sheathes the anode for this. It is advantageous when the cathode is grounded here.

The air ionization module has a support made up of a mounting plate and a circuit board that are thermally insulated vis-a-vis one another. The circuit board is comprised of an electrical insulator on the conductor paths and contact points made of an electrically conductive material are possibly applied in a familiar way. The element made of a thermally insulating material is located between these two plates. It is advantageous that no thermal bridge therefore exists between these two plates. Furthermore, the material is also not flammable, in particular, so smoldering fires can also be prevented. The element can be advantageously made of a plastic for this, in particular a polyisocyanurate (PIR) or a polyurethane (PU). The air ionization module is a component of the incoming-air channel in a familiar way. The support can simultaneously be a component of a wall of the incoming-air channel here. Assembly and disassembly are substantially simplified. That is especially advantageous with regard to cleaning and maintenance work, especially of the ionization tubes. The arrangement in the wall of the incoming-air channel saves space. Furthermore, at least one air ionization module can be in the incoming-air channel or in the air-conditioning system itself. Moreover, at least one air ionization module can be in the incoming-air channel. The ionization tubes project into the channel space and therefore into the incoming-air flow. If cooled air is supplied when higher temperatures otherwise prevail, condensation of water is prevented with the use of an air ionization module with a lacking heat bridge in the support. Danger that otherwise results form the condensing water and the ionization tubes operating with high voltage is prevented. The air ionization module can therefore also be safely operated when there are higher air temperatures and relative humidity levels. The service life of the module is increased because of that.

Advantageous design forms of the invention are specified in claims 2 to 11.

According to the further design form of claim 2 the element made of the thermally insulating material is located between the plates and a wall made of a material that is at least in parts thermally insulating surrounds this element. The plates and the wall therefore form a compact unit. The element can be made of the most diverse materials; it can also be an element made of an elastic material.

According to the further design form of claim 3, the plates are connected to one another via latching mechanisms; latching elements engage in recesses here. Assembly and also disassembly are therefore easy.

The mounting plate according to the further design form of claim 4 is larger than the circuit board. The air ionization module can therefore be easily integrated into a wall of the channel without forming a heat bridge. This can be done via a spaced-apart arrangement between the circuit board and a channel wall. An element made of a material that is not thermally insulating can, of course, also bridge the gap between the circuit board and a channel wall.

According to the further design form of claim 5, the mounts are located in the element made of thermally insulating material, so they are flush with the surface of the circuit board pointing outwards.

According to the further design form of claim 6, the mounts are electrically connected to conducting paths of the circuit board and thereby simultaneously attached. The anodes of the ionization tubes are connected to one another via mounts and conducting paths of the circuit board. At least one component of an electrical connection element for a removable connection of at least one cathode to at least one conducting path of the circuit board is connected in an electrically conductive manner and thereby simultaneously attached. The anodes and cathodes of ionization tubes that are connected to one another are a group of ionization tubes.

The anodes of the ionization tubes of one group are, according to the further design form of claim 7, interconnected to the secondary winding of a transformer. The primary winding of the transformer can be connected to a low-voltage electrical mains line via a switch. Furthermore, the cathodes of the ionization tubes are grounded.

According to the further design form of claim 8, the actuation unit of a switch that operates mechanically or the control electrode of a switch that is controlled electrically is connected to a data-processing system, so there is automatic and/or pre-specified operation of the ionization tubes via the data-processing system.

Transformers for groups of ionization tubes are, according to the further design form of claim 9, arranged in a housing. The housing, moreover, is fastened to the mounting plate, so the ionization tubes, the support and the housing are a compact air ionization module.

The element made of thermally insulating material between the mounting plate and the circuit board is comprised, according to the further design form of claim 10, of an expanded plastic. The plastic is simply put into the space between these plates for this and forms itself during the curing process; bubbles filled with air also arise, so there is good insulation between the plates. At the same time, the existing space can be completely filled out in a simple way.

It is convenient, according to the further design form of claim 11, that four ionization tubes are a group of ionization tubes. Furthermore, they are advantageously arranged at the corner points of a parallelogram with no right angles. Ionization tubes are therefore arranged at an offset to one another, so there is an optimal air flow of the ionization tubes.

An example of the invention is shown in the drawings in the form of its basic structure in each case, and it will be described in more detail below.

BRIEF DESCRIPTION OF THE DRAWINGS

The following are shown in the figures.

DETAILED DESCRIPTION OF THE PREFERRED EMBODIMENT

An air ionization module is essentially comprised of a support 1 with ionization tubes 2 and a housing 3 for transformers 8.

Figure 1:
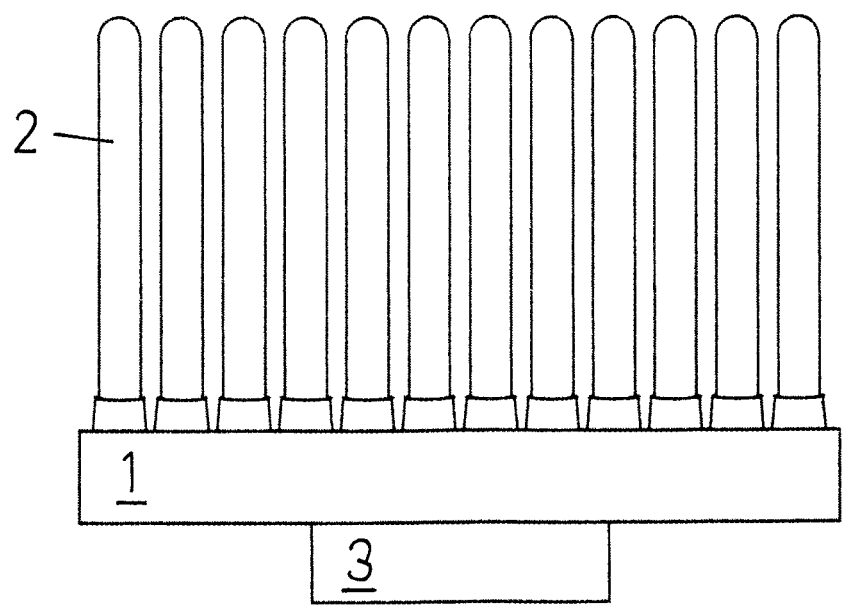
FIG. 1 shows an air ionization module in a side view.
Figure 2:
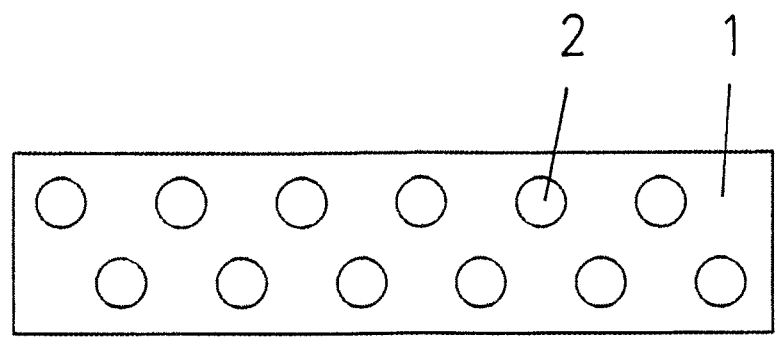
FIG. 2 shows an air ionization module in a top view.

The following are shown with regard to this:
FIG. 1 shows an air ionization module in a basic side view and
FIG. 2 shows an air ionization module in a basic top view.

The support 1 has two plates 4, 5 spaced apart from one another; a first plate 4 is a mounting plate 4 and a second plate 5 is a circuit board 5. An element 6 made of a thermally insulating material is located between the plates 4, 5, so the second plate 5 is arranged in a thermally insulating manner vis-a-vis the first plate 4. The mounting plate 4 is designed to be larger than the circuit board 5. The mounting plate 4 and/or the circuit board 5 can also have a U shape in certain embodiments. The element 6 made of the thermally insulating material is comprised of an expanded plastic. The mounting plate 4 is a metal plate 4, whereas the circuit board 5 is, in a familiar fashion, a plate 5 made of an electrical insulator with applied conducting paths.

Figure 3:
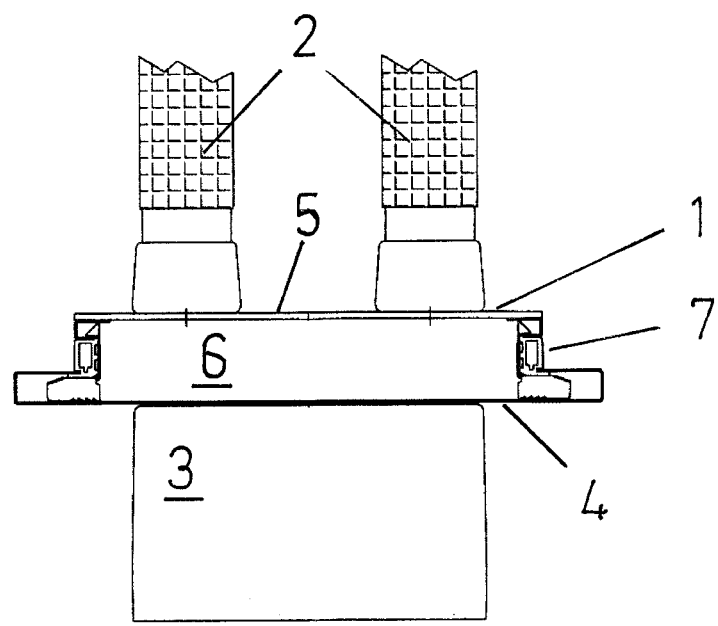
FIG. 3 shows a support with ionization tubes and a housing for transformers and
FIG. 4 a circuit with ionization tubes.

FIG. 3 shows with regard to this a support 1 with ionization tubes 2 and a housing 3 for transformers in a basic diagram.

The element 6 made of the thermally insulating material is located between the plates 4, 5 and a wall 7 surrounding this element 6. The latter is comprised, at least in certain areas, of a thermally insulating material, preferably plastic. The wall 7 advantageously has latching mechanisms at the same time; latching elements engage in recesses here.

The ionization tubes 2 are arranged in mounts in a removable fashion.

The circuit board 5 has the mounts; the anodes of the ionization tubes 2 are connected to one another via the mounts and conductor paths of the circuit board 5. At the same time, connection elements for the cathodes of the ionization tubes 2 are arranged on or in the circuit board 5, so the cathodes of the ionization tubes 2 are connected with one another via connection elements and conducting paths. The cathodes are removably connected via cables to the connection elements with screw connections for this. The anodes and cathodes of ionization tubes 2 that are connected with one another are interconnected to form a group of ionization tubes 2. To this end, a group of ionization tubes 2 can be comprised, as an example, of four ionization tubes 2 that are arranged at the corner points of a parallelogram with no right angles.

The mounts are connected to the circuit board 5 in such a way that they are flush with the surface of the circuit board 5 pointing outwards.

The anodes of the ionization tubes 2 of a group are interconnected with the secondary winding of a transformer 8. The primary winding of the transformer 8 can be connected via a switch 9 to a low-voltage electrical mains line 10. The cathodes of the ionization tubes 2 are grounded.

Figure 4:
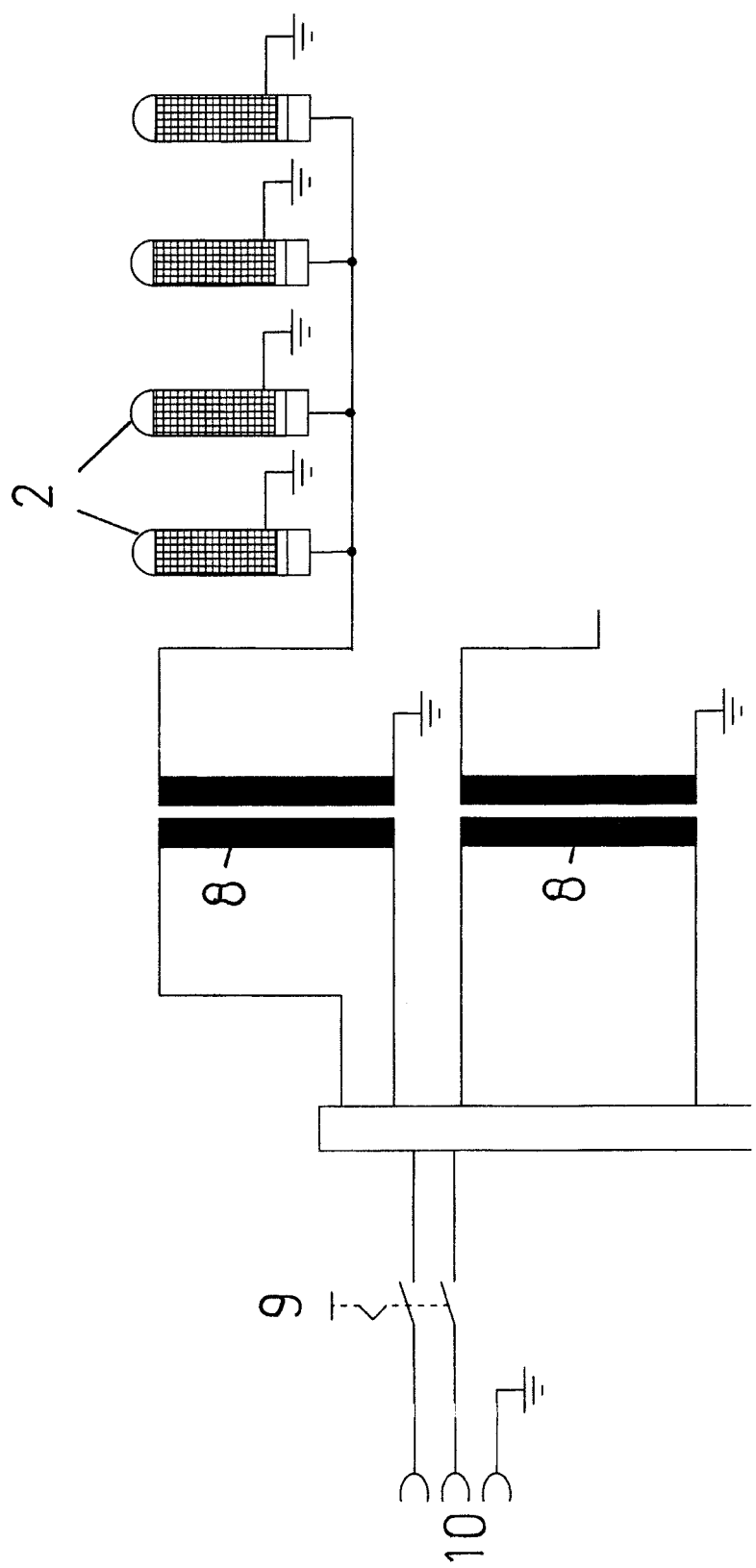

FIG. 4 shows a circuit with ionization tubes 2 in a basic diagram.

The transformers 8 for the groups of ionization tubes 2 are located in the housing 3 that, moreover, is fastened to the mounting plate 4. The ionization tubes 2, the support 1 and the housing 3 with the transformers 8 are therefore a compact air ionization module.

The actuation unit of a switch that operates mechanically or the control electrode of a switch 9 that is controlled electrically is connected to a data-processing system, so there is automatic and/or pre-specified operation of the ionization tubes 2.

LIST OF REFERENCE NUMERALS

1 Support
2 Ionization tube
3 Housing
4 Mounting plate
5 Circuit board
6 Element made of thermally insulating material
7 Wall
8 Transformer
9 Switch
10 Mains line

The invention claimed is:

1. Air ionization module with ionization tubes removably arranged in mounts and a support with the mounts, characterized in that the support (1) has two plates (4, 5) spaced apart from one another, wherein a first plate (4) is a mounting plate (4) and a second plate (5) is a circuit board (5) with the mounts and that an element (6) made of thermally insulating material is located between the plates (4, 5) so that the second plate (5) is thermally insulating vis-a-vis the first plate (4).

2. Air ionization module according to claim 1, characterized in that the element (6) made of thermally insulating material is located between the plates (4, 5) and a wall (7) surrounding this element (6) that is made at least in sections of thermally insulating material.

3. Air ionization module according to claim 1, characterized in that the plates (4, 5) are connected with one another via latching mechanisms, wherein latching elements engage in recesses.

4. Air ionization module according to claim 1, characterized in that the mounting plate (4) is larger than the circuit board (5).

5. Air ionization module according to claim 1, characterized in that the mounts are located in the element (6) made of the thermally insulating material so that they are flush with the surface of the circuit board (5) pointing outwards.

6. Air ionization module according to claim 1, characterized in that the mounts are electrically connected to conducting paths of the circuit board (5) and are thereby simultaneously attached, that anodes of the ionization tubes (2) are connected with one another via mounts and conductor paths of the circuit board (5), that at least one component of an electrical connection element for a removable connection of at least one cathode to at least one conducting path of the circuit board (5) is connected in an electrically conductive manner and thereby simultaneously attached, and that the anodes and cathodes of ionization tubes (2) that are connected to one another are a group of ionization modules (2).

7. Air ionization module according to claim 1, characterized in that the anodes of the ionization tubes (2) of a group are interconnected to a secondary winding of a transformer (8), that the a primary winding of the transformer (8) can be connected to a low-voltage electrical mains line (10) via a switch (9) and that the cathodes of the ionization tubes (2) are grounded.

8. Air ionization module according to claim 7, characterized in that an actuation unit of a switch that operates mechanically or the control electrode of a switch (9) that is controlled electrically is connected to a data-processing system, so there is automatic and/or pre-specified operation of the ionization tubes (2) via the data-processing system.

9. Air ionization module according to claim 1, characterized in that transformers (8) for groups of ionization tubes (2) are arranged in a housing (3) and that the housing (3) is fastened to the mounting plate (4) so that the ionization tubes (2), the support (1) and the housing (3) are a compact air ionization module.

10. Air ionization module according to claim 1, characterized in that the element (6) made of thermally insulating material between the mounting plate (4) and the circuit board (5) is comprised of an expanded plastic.

11. Air ionization module according to claim 1, characterized in that four ionization tubes (2) are a group of ionization tubes (2) and that the ionization tubes (2) are arranged at the corner points of a parallelogram with no right angles.

* * * * *